United States Patent
Higgins et al.

(10) Patent No.: US 11,382,892 B2
(45) Date of Patent: Jul. 12, 2022

(54) METHOD FOR ADMINISTRATION

(71) Applicant: Hoffmann-La Roche Inc., Nutley, NJ (US)

(72) Inventors: Brian Higgins, Fresh Meadows, NY (US); Gwen Nichols, New York, NY (US); Lin-Chi Chen, New York, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 31 days.

(21) Appl. No.: 16/519,516

(22) Filed: Jul. 23, 2019

(65) Prior Publication Data
US 2020/0085788 A1 Mar. 19, 2020

Related U.S. Application Data

(63) Continuation of application No. 14/673,153, filed on Mar. 20, 2015, now abandoned, which is a continuation of application No. 14/217,929, filed on Mar. 18, 2014, now abandoned, which is a continuation-in-part of application No. 13/759,647, filed on Feb. 5, 2013, now abandoned.

(60) Provisional application No. 61/612,429, filed on Mar. 19, 2012.

(51) Int. Cl.
| A61K 31/40 | (2006.01) |
| A61K 9/14  | (2006.01) |
| A61K 9/10  | (2006.01) |
| A61K 9/28  | (2006.01) |

(52) U.S. Cl.
CPC ............... *A61K 31/40* (2013.01); *A61K 9/10* (2013.01); *A61K 9/146* (2013.01); *A61K 9/284* (2013.01)

(58) Field of Classification Search
CPC .......... A61K 31/40; A61K 9/10; A61K 9/146; A61K 9/284
See application file for complete search history.

(56) References Cited

U.S. PATENT DOCUMENTS 9,216,170 B2   12/2015  Higgins et al.
2010/0152190 A1*  6/2010  Bartkovitz ........... C07D 409/04
                                                         514/237.2

FOREIGN PATENT DOCUMENTS

WO    2008076415 A1    6/2008
WO    2011098398 A1    8/2011

OTHER PUBLICATIONS

Sbar et al. Cancer Investigation (2002) vol. 20, pp. 644-650 (Year: 2002).*
The English translation of the Korean Office Action, dated Nov. 2, 2020, in the related Korean Appl. No. 2019-7008801.
Terry Priestman, "Cancer Chemotherapy in Clinical Practice," Springer, 2008, pp. 24 to 27.
The English translation of the Brazilian Examination Report, dated Sep. 20, 2021, in the related Brazilian Appl. No. 12 2020 002189-6.
Van Winkle et al., "Ifosfamide, Carboplatin, and Etoposide (ICE) Reinduction Chemotherapy in a Large Cohort of Children and Adolescents With Recurrent/Refractory Sarcoma: The Children's Cancer Group (CCG) Experience," Pediatr Blood Cancer 2005;44:338-347.

(Continued)

*Primary Examiner* — San Ming R Hui

(57) ABSTRACT

There is provided a new dosage regimen for Compound A which maximizes anti-tumor activity while maintaining acceptable toxicity levels.

11 Claims, 3 Drawing Sheets

(56) References Cited

OTHER PUBLICATIONS

Makino et al., "Comparative study between daily and 5-days-a-week administration of oral 5-fluorouracil chemotherapy in mice: determining the superior regimen," Cancer Chemother Pharmacol (2001) 48: 370-374.
The English translation of the Chinese Office Action, dated Jul. 13, 2021, in the related Chinese Appl. No. 201910030832.0.
The English translation of the Chinese Office Action, dated Mar. 11, 2022, in the related Chinese patent application No. 201910030832.0.

* cited by examiner

METHOD FOR ADMINISTRATION

CROSS-REFERENCE TO RELATED APPLICATIONS

This application is a Continuation of application No. 14/673,153, filed Mar. 30, 2015, which is a Continuation of application No. 14/217,929, filed Mar. 18, 2014, which is a Continuation-in-Part of application No. 13/759,647, filed Feb. 5, 2013, which claims the benefit of U.S. Provisional Application No. 61/612,429, filed Mar. 19, 2012. Each of these applications is incorporated by reference herein in its entirety.

FIELD OF THE INVENTION

The present invention is related to improved methods of administration of 4-{[(2R,3S,4R,5S)-4-(4-Chloro-2-fluoro-phenyl)-3-(3-chloro-2-fluoro-phenyl)-4-cyano-5-(2,2-dim-ethyl-propyl)-pyrrolidine-2-carbonyl]-amino}-3-methoxy-benzoic acid (referred to herein as Compound A) in the treatment of cancer in humans. In particular, the invention relates to improved methods of administration of Compound A that provide desirable antineoplastic effects with a tolerable level of toxicity. The methods of the invention are characterized by administering specific doses of Compound A under a specific protocol which elicits effective and best tolerated biological activity in human patients. This protocol is expected to be safer and at least as effective as, possibly more effective than, administering more frequent doses at lower concentrations or larger doses at intermittent periods.

BACKGROUND OF THE INVENTION

P53 is a tumor suppressor that regulates cell cycle, apoptosis, DNA repair and cell death. In human cancer, the p53 transcription factor is typically inactive leading to uncontrolled cell growth. Inhibition of p53 activity occurs through binding of MDM2 to p53. Selective inhibition of the MDM2-p53 interaction activates the p53 pathway and induces cell cycle arrest and apoptosis. Compound A is an orally administered pyrrolidine that inhibits the binding of MDM2 to p53 and is thus useful in the treatment of cancer. It has the following chemical structure:

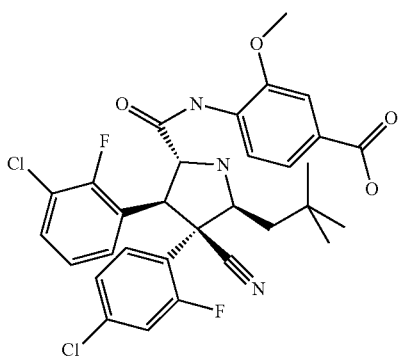

Molecular Weight = 616.4973
Molecular Formula = C31H29Cl2F2N3O4

Compound A recently entered into phase I clinical trials for the treatment of solid tumors. See ClinicalTrials.gov, identifier NCT01462175. This compound is disclosed in US Pub 2010/0152190 A1. To the extent necessary, this patent publication is herein incorporated by reference.

Applicants have discovered that Compound A is especially effective, and best tolerated, in human cancer therapy when administered in the specific doses and pursuant to the specific protocols herein described.

SUMMARY OF THE INVENTION

The present invention relates to a method of treating a patient suffering with cancer, in particular colon, breast, prostate, head and neck, lung or kidney cancer, leukemia, melanoma, soft tissue sarcoma or osteosarcoma, comprising administering to the patient Compound A in an amount of from about 800 to about 3000 mg/day, or from about 1000 to about 2500 mg/day, or from about 1250 to about 1800 mg/day, for an administration period of up to about 7 days, preferably up to about 5 days, on days 1-7, or preferably days 1-5, of a 28 day treatment cycle, followed by a rest period of from about 21 to about 23 days, preferably up to about 23 days.

The present invention further relates to a method of treating a patient suffering from cancer, in particular colon, breast, prostate, head and neck, lung or kidney cancer, leukemia, melanoma, or soft tissue sarcoma, osteosarcoma comprising administering to the patient a low concentration of Compound A in an amount of from about 400 to about 1600 mg/day for an administration period of up to about 7 days, preferably up to about 5 days, on days 1-7, or preferably days 1-5, of a 28 day treatment cycle, followed by a rest period of from about 21 to about 23 days, preferably about 23 days.

The present invention further relates to a method of treating a patient suffering from cancer comprising administering to the patient Compound A in an amount from about 400 mg/day to about 1200 mg/day for up to about 7 days preferably 5 days, followed by a rest period of about 21-23 days, of a 28 day treatment cycle.

The present invention further relates to a method of treating a patient suffering from cancer comprising administering to the patient Compound A in an amount of from about 400-1000 mg/day for about 3 days followed by a rest period of about 25 days of a 28 day treatment cycle.

The present invention further relates to a method of treating a patient suffering from cancer comprising administering to the patient Compound A in an amount of from 1600-2400 mg/once weekly×3 weeks followed by about 13 days of rest, said administration starting on the first day of a 28 day treatment cycle.

The present invention further relates to a method of treating a patient suffering from cancer, comprising administering to said patient a pharmaceutical composition containing as an active ingredient Compound A at about 500 mg/day total, daily for up to about 5 days, followed by a rest period of about 23 days, said administration starting on the first day of a 28 day treatment cycle.

The present invention further relates to a method of treating a patient suffering from leukemia, comprising administering to said patient a pharmaceutical composition containing as an active ingredient Compound A at about 1200 mg total daily, for up to about 5 days, followed by a rest period of about 23 days, said administration starting on the first day of a 28 day treatment cycle.

DETAILED DESCRIPTION OF THE INVENTION

Figure 1:
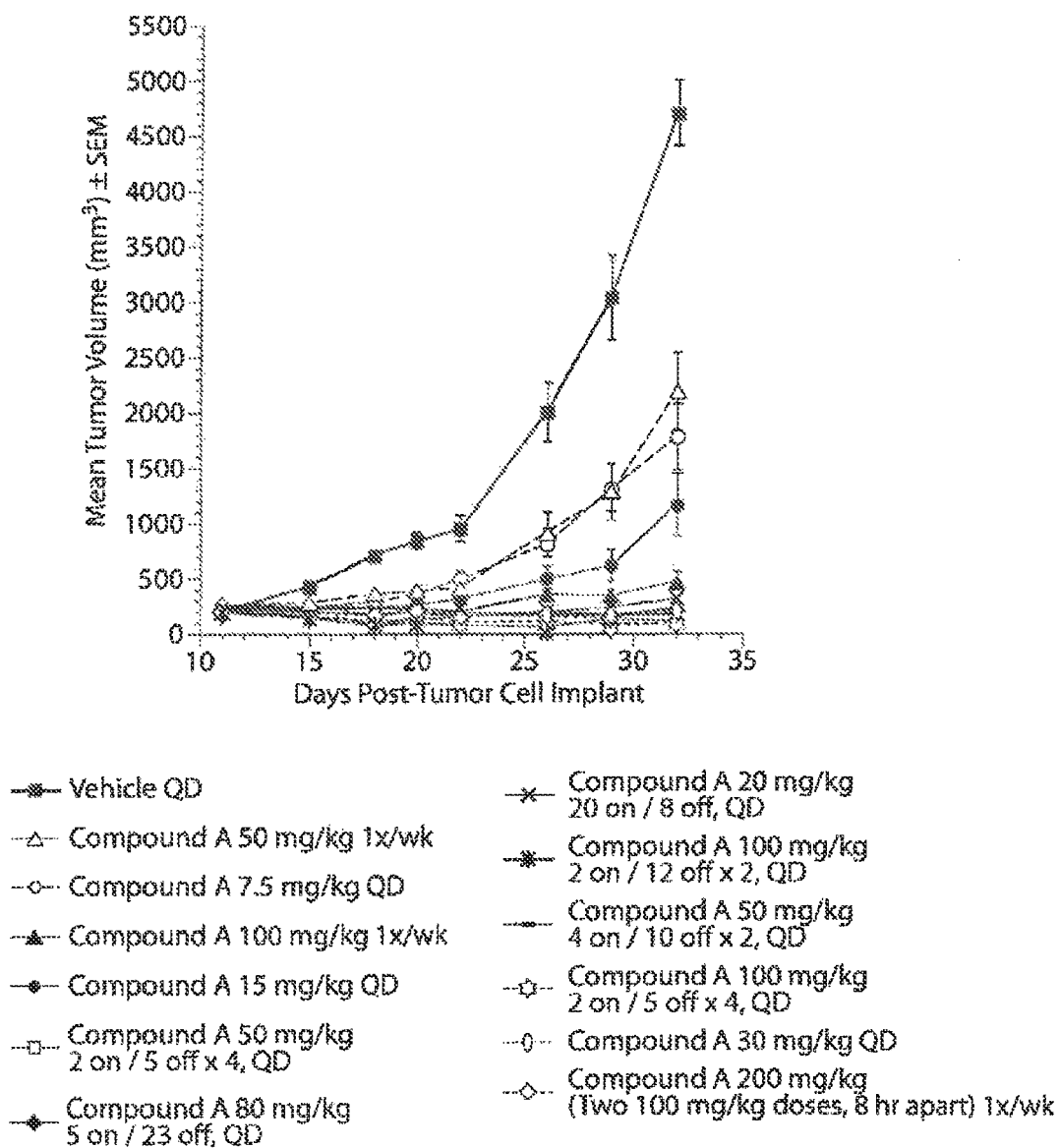
FIG. 1 illustrates the antitumor activity, as demonstrated by the change in mean tumor volume over time, of Compound A monotherapy for a number of different dosing schedules, including a continuous 5 day dosing schedule.

"Tumor control" means that the perpendicular diameters of measurable lesions have not increased by 25% or more from the last measurement. See, e.g., World Health Organization ("WHO") Handbook for Reporting Results of Cancer Treatment, Geneva (1979). The determination of tumor control or shrinkage (also referred to as "regression") is made by known methods. For example, by evaluation of patient symptoms, physical examination, X-ray, MRI or CAT scan or other commonly accepted evaluation modalities.

The present invention relates to a method of treating a patient suffering with cancer, in particular colon, breast, prostate, head and neck, lung or kidney cancer, leukemia, melanoma, soft tissue sarcoma or osteosarcoma, comprising administering to the patient Compound A in an amount of from about 400 to about 1600 mg/day, or from about 400 to about 1200 mg/day, for an administration period of up to about 7 days, preferably up to about 5 days, on days 1-7, or preferably days 1-5, of a 28 day treatment cycle, followed by a rest period of from about 21 to about 23 days, preferably up to about 23 days. The course of a preferred cycle is about 28 days, though cycles anywhere between about 14 and about 28 days are contemplated. This treatment cycle is repeated for as long as the tumor remains under control and the regimen is clinically tolerated.

Dosages of Compound A can be applied either as a body surface area ("BSA") adapted dose (mg/m$^2$/day) or following flat dosing (mg/day). Compound A may be administered as a single dose daily or divided into multiple daily doses.

A patient's body measurement in square meters ("m$^2$") typically ranges from about 1.4 m$^2$ to about 2.2 m$^2$. Thus, the total amount of Compound A to be delivered in a treatment cycle (mg) using a BSA adapted dose would be calculated as follows:

[Dose intensity(mg/m$^2$/week)]×[BSA(m)]×[number of weeks in treatment cycle].

In an embodiment, Compound A is administered daily for about 5 days, on days 1-5 of a treatment cycle, followed by a rest period of 23 days ("5+/23−"). The 5+/23− treatment schedule is expected to be superior to interim schedules or to longer schedules as currently on-going Phase I studies indicate that in solid tumors, maximal apoptosis occurs only after about 48 hours of continuous exposure and longer schedules seem to present occurrence of delayed thrombocytopenia ("TCP"). Thus, a 3-5 daily treatment schedule is expected to provide the best benefit ratio taking into consideration efficacy and toxicity.

In the present invention, the patient is administered a lower dose of Compound A in an amount from about 400 to about 1600 mg/day for an administration period of up to about 7 days preferably about 5 days, on days 1-7, or preferably days 1-5, of a 28 day treatment cycle. It has been unexpectedly found that it is at least as effective and safer to treat humans with lower and less frequent doses of Compound A than administering frequent doses at lower concentrations or larger doses at intermittent periods. It has been found that the dosing regimens are effective in eliciting biological response from patients and better tolerated in terms of safety.

Compound A is administered daily, either once or twice (bid) daily. The compound is administered to the patient in an oral unit dosage form, most preferably in tablet form.

Preferably, the 5 day treatment schedule is repeated every twenty-eight days, or as soon as permitted by recovery from toxicity, for so long as the tumor is under control or regressing and the patient tolerates the regimen. Preferably, these treatment cycles are repeated for up to about 12 cycles.

In an embodiment, Compound A is administered daily in an amount from about 400 to about 1600 mg/day for up to about 5 days on days 1-5 of a 28 day cycle.

In another embodiment, Compound A is administered in an amount from about 400 mg/day to about 1200 mg/day, daily, for about 5 days, followed by a rest period of up to about 23 days, said administration starting on the first day of a 28 day treatment cycle.

In another embodiment, Compound A is administered daily in an amount from about 400-1000 mg/day for up to about 3 days followed by 25 days of rest of a 28 day cycle.

In another embodiment, Compound A is administered once weekly in an amount from 1600-2400 mg/week for 3 weeks followed by about 13 days of rest of a 28 day schedule.

In another embodiment Compound A is administered to treat advance solid tumors including colon, breast, prostate, head, neck, lung, kidney, melanoma, soft tissue sarcoma or osteosarcoma at about 500 mg/day total, daily for up to about 5 days, followed by a rest period of about 23 days, said administration starting on the first day of a 28 day treatment cycle.

In another embodiment Compound A is administered to treat leukemia at about 600 mg/day two times a day, for up to about 5 days, followed by a rest period of about 23 days, said administration starting on the first day of a 28 day treatment cycle.

The present invention may be exemplified by controlled preclinical animal studies as shown in the Examples below, which illustrates the invention without limitation.

The present invention is further exemplified by clinical studies in humans as shown in the examples below which illustrate the invention without limitation.

EXAMPLES

The superiority of the 5 day, 3 day and weekly dosing regimen of the present invention on solid tumors is demonstrated by the following experiments.

Abbreviations used herein are as follows:
x times
po orally
bid twice daily
wk week
qd once daily
qd×5 once daily for five days
qweekly or 1×/wk once a week
BWL body weight loss
SD standard deviation
Toxicity In the examples below, weight loss was graphically represented as percent change in mean group body weight, using the formula: $((W-W_0)/W_0) \times 100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group. Toxicity is defined as ≥20% of mice in a given group demonstrating ≥20% body weight loss and/or death.

Tumor Growth Inhibition (TGI) and Assessment of Survival/Increase in Life Span (ILS)

Efficacy data was graphically represented as the mean tumor volume*standard error of the mean (SEM). In addition, tumor volumes of treated groups were presented as percentages of tumor volumes of the control groups (% T/C), using the formula: $100 \times ((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment.

Tumor volume (in cubic millimeters) was calculated using the ellipsoid formula: $(D \times (d^2))/2$, where "D" represents the large diameter of the tumor and "d" represents the small diameter. In some cases, tumor regression and/or percent change in tumor volume was calculated using the formula: $((T-T_0)/T_0) \times 100$, where 'T' represents mean tumor volume of the treated group at a particular day, and '$T_0$' represents mean tumor volume of the same treated group at initiation of treatment.

Statistical analysis was determined by the rank sum test and One Way Anova and a post-hoc Bonferroni t-test (SigmaStat, version 2.0, Jandel Scientific, San Francisco, Calif., USA). Differences between groups were considered to be significant when the probability value (p) was ≤0.05.

For survival assessment, the percent of increased life space (ILS) was calculated as: 100×[(median survival day of treated group−median survival day of control group)/median survival day of control group]. Median survival was determined utilizing Kaplan Meier survival analysis. Survival in treated groups was statistically compared with the vehicle group and survival comparisons were done between groups using the log-rank test (Graph Pad Prism, La Jolla, Calif., USA). Differences between groups were considered significant when the probability value (p) was ≤0:05.

Example 1

The antitumor activity of Compound A in the human osteosarcoma cancer xenograft model SJSA1 in immunocompromised mice using a variety of different schedules was assessed.

A. Test Compound A

Compound A was formulated as an amorphous solid dispersion micro-bulk precipitate (MBP) powder containing 30% drug substance and 70% HPMC-AS polymer was reconstituted immediately before administration as a suspension in Klucel/Tween, and remaining suspension was discarded after dosing. All dose levels are reported as the actual dosage of Compound A rather than including drug plus polymer.

B. In Vivo Assays

Animals

Female athymic Crl:NU-Foxn1nu mice (10/group), obtained from Charles River Laboratories (Wilmington, Del.) were utilized when they were approximately 10-12 weeks of age and weighed 23-25 g. The health of the mice was assessed daily by gross observation and analyses of blood samples taken from sentinel animals housed on shared shelf racks. All animals were allowed to acclimate and recover from any shipping-related stress for a minimum of 72 hours prior to experimental use. Autoclaved water and irradiated food (5058-ms Pico Lab mouse chow, Purina Mills, Richmond, Ind.) were provided ad libitum, and the animals were maintained on a 12 hour light and dark cycle. Cages, bedding and water bottles were autoclaved before use and changed weekly. All animal experiments were conducted in accordance with the Guide for the Care and Use of Laboratory Animals, local regulations, and protocols approved by the Roche Animal Care and Use Committee in an AAALAC accredited facility.

Tumors

SJSA cells (ATCC) were maintained in RPMI 1640+10% (v/v) heat-inactivated FBS+i % (v/v) 200 nM L-glutamine. Each mouse received $5 \times 10^6$ cells in a 1:1 mixture of phosphate buffered saline and Matrigel in a total volume of 0.2 ml. Cells were implanted subcutaneously in the right flank using a 1 cc syringe and a 26 gauge needle.

Study Design:

The doses selected for Compound A and schedules utilized in this study are shown in Table 1 below.

TABLE 1

Study Design

| Tumor Model | Treatment Groups |
|---|---|
| SJSA | 1. Vehicle qd po |
| | 2. Compound A 7.5 mg/kg qd po |
| | 3. Compound A 15 mg/kg qd po |
| | 4. Compound A 30 mg/kg qd po |
| | 5. Compound A 20 mg/kg 20 days qd po, 8 days off |
| | 6. Compound A 50 mg/kg 1×/week po |
| | 7. Compound A 100 mg/kg 1×/week po |
| | 8. Compound A 200 mg/kg (given as two 100 mg/kg doses 8 hours apart (bid)), 1×/week po |
| | 9. Compound A 50 mg/kg 4 days qd po, 10 days off × 2 cycles |
| | 10. Compound A 50 mg/kg 2 days qd po, 5 days off × 4 cycles |
| | 11. Compound A 100 mg/kg 2 days qd po, 5 days off × 4 cycles |
| | 12. Compound A 80 mg/kg 5 days qd po, 23 days off |
| | 13. Compound A 100 mg/kg 2 days qd po, 12 days off × 2 cycles |

Treatment

Compound A was administered orally (po) using a 1 cc syringe and 18-gauge gavage needle (0.2 ml/animal). Treatment duration was 2-4 weeks. Dates of tumor implant, treatment initiation (study start date), and termination of treatment (study end date) can be found in Table 6 below. The starting tumor volume for this study was about 220 mm³. Tumor volumes and animal body weights were measured three times per week and animals were monitored for clinical signs daily.

Figure 2:
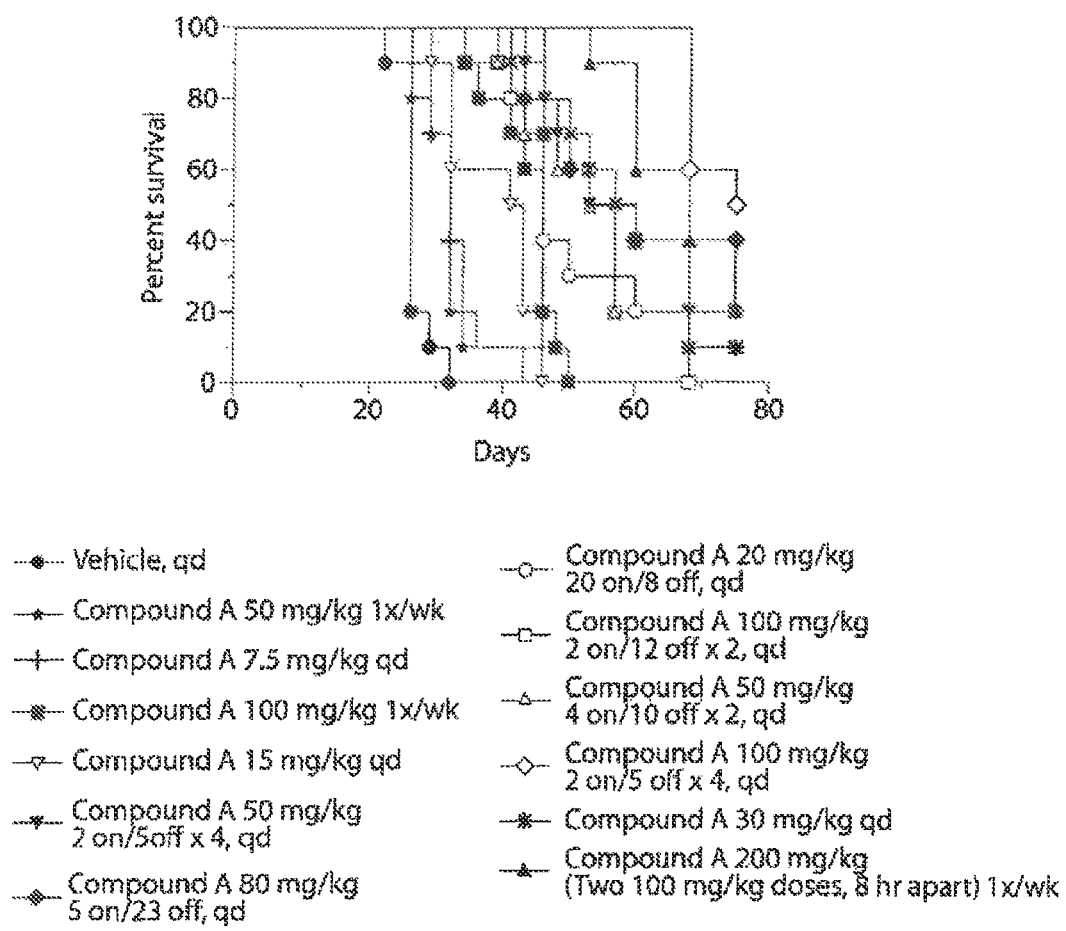
FIG. 2 shows the increased lifespan of mice treated with Compound A for the different dosing schedules also reflected in FIG. 1.

The results of this experiment are summarized Tables 1-3 below and FIGS. 1 and 2. As can be seen, the 5 day treatment schedule yielded the greatest percent increase in life span (% ILS) as well as high percent tumor growth inhibition (% TGI) with reasonable toxicity. FIG. 1 also shows good growth inhibitory activity of the 5 day on/23 day off treatment schedule.

TABLE 2

Toxicity Summary

| Group | Frequency | % Change in Body Weight at end of Study Day 29 | Maximum % Weight loss | Maximum % Weight gain | # of animals ≥20% BWL | Mortality |
|---|---|---|---|---|---|---|
| Vehicle | QD | 13.0 | −1.2 | 13.0 | 0 | 0 |
| Compound A 100 mg/kg | 1x/wk | 9.1 | 4.2 | 9.1 | 0 | 0 |
| Compound A 200 mg/kg (Two 100 mg/kg doses, 8 hr apart) | 1x/wk | 6.3 | 1.9 | 6.3 | 0 | 0 |
| Compound A 50 mg/kg | 2 on/5 off x 4, QD | 7.1 | −0.8 | 7.1 | 0 | 0 |
| Compound A 80 mg/kg | 5 on/23 off, QD | 8.0 | 0.3 | 8.0 | 0 | 0 |
| Compound A 20 mg/kg | 20 on/8 off, QD | 1.2 | −3.9 | 1.2 | 0 | 0 |
| Compound A 100 mg/kg | 2 on/12 off x 2, QD | 0.9 | −0.6 | 1.8 | 0 | 0 |
| Compound A 50 mg/kg | 4 on/10 off x 2, QD | 1.2 | −1.1 | 1.2 | 0 | 0 |
| Compound A 15 mg/kg | QD | 5.9 | −2.2 | 5.9 | 0 | 0 |
| Compound A 100 mg/kg | 2 on/5 off x 4, QD | 1.3 | −2.8 | 1.3 | 0 | 0 |
| Compound A 30 mg/kg | QD | 1.3 | −0.2 | 1.3 | 0 | 0 |
| Compound A 50 mg/kg | 1 x/wk | 6.6 | −0.3 | 6.6 | 0 | 0 |
| Compound A 7.5 mg/kg | QD | 9.0 | −0.3 | 9.0 | 0 | 0 |

TABLE 3

Efficacy Summary (left side)

| Group Vehicle or Compound A | Frequency | Mean Tumor (mm3) Start Study Day: 11 | SEM | SD | Mean Tumor Volume (mm3) End Study Day: 32 | SD | SEM |
|---|---|---|---|---|---|---|---|
| Vehicle | QD | 215.03 | ±19.00 | ±60.08 | 4696.49 | ±785.28 | ±296.91 |
| 50 mg/kg | 1x/week | 275.41 | ±22.66 | ±71.65 | 22.66 | ±1103.00 | ±348.80 |
| 7.5 mg/kg | QD | 240.88 | ±18.01 | ±56.95 | 18.01 | ±956.45 | ±302.46 |
| 100 mg/kg | 1 x/week | 193.61 | ±9.67 | ±30.57 | 474.73 | ±273.78 | ±86.58 |
| 15 mg/kg | QD | 232.37 | ±16.42 | ±51.93 | 16.42 | ±872.83 | ±276.01 |
| 50 mg/kg | 2 on/5 off x 4, QD | 203.43 | ±18.78 | ±59.39 | 257.29 | ±102.12 | ±32.29 |
| 80 mg/kg | 5 on/23 off, QD | 197.38 | ±12.80 | ±40.48 | 128.05 | ±84.89 | ±26.84 |
| 20 mg/kg | 20 on/8 off, QD | 207.20 | ±16.97 | ±53.67 | 315.19 | ±277.51 | ±87.76 |
| 100 mg/kg | 2 on/12 off x 2, QD | 201.40 | ±9.86 | ±31.18 | 179.88 | ±154.02 | ±48.71 |
| 50 mg/kg | 4 on/10 off x 2, QD | 213.61 | ±12.09 | ±38.23 | 244.70 | ±240.07 | ±75.92 |
| 100 mg/kg | 2 on/50 off x 4, QD | 190.78 | ±25.68 | ±81.22 | 25.68 | ±15.82 | ±5.00 |
| 30 mg/kg | QD | 250.86 | ±19.35 | ±61.19 | 19.35 | ±159.01 | ±50.28 |
| 100 mg/kg | 200 mg/kg (Two 100 mg/kg doses, 8 hr apart) x 1x | 224.88 | ±12.02 | ±38.02 | 158.95 | ±68.86 | ±21.78 |

TABLE 3

Efficacy Summary Continued (right side)

| % T/C End of Study Day: 32 | % Inhibition end of study Day: 32 | p value end of study Day: 32 | Average % Regression per Group | Partial Regression | Full Regression | Animals per Group | % Increased Life Span | p Value versus Vehicle |
|---|---|---|---|---|---|---|---|---|
| — | — | — | — | 0 | 0 | 7 | — | — |
| 43 | 57 | <0.001 | — | 0 | 0 | 10 | 23 | 0.0036 |
| 34 | 66 | <0.001 | — | 0 | 0 | 10 | 23 | 0.0012 |
| 6 | 94 | <0.001 | — | 1 | 0 | 10 | 77 | <0.0001 |
| 21 | 79 | <0.001 | — | 0 | 0 | 10 | 62 | <0.0001 |
| 1 | 99 | <0.001 | — | 3 | 0 | 10 | 119 | <0.0001 |
| -2 | regression | <0.001 | 35 | 6 | 2 | 10 | 127 | <0.0001 |
| 2 | 98 | <0.001 | — | 5 | 0 | 10 | 77 | <0.0001 |
| 0 | regression | <0.001 | 11 | 7 | 0 | 10 | 119 | <0.0001 |
| 1 | 99 | <0.001 | — | 6 | 0 | 10 | 112 | <0.0001 |
| -2 | regression | <0.001 | 47 | 9 | 0 | 10 | 188 | <0.0001 |
| -1 | regression | <0.001 | 13 | 7 | 0 | 10 | 127 | <0.0001 |
| -1 | regression | <0.001 | 29 | 7 | 0 | 10 | 162 | <0.0001 |

TABLE 4

Survival Summary

| Group | | 50% Treatment Days | 50% Vehicle days | % ILS | p value |
|---|---|---|---|---|---|
| Vehicle | QD | — | — | — | — |
| Compound A 100 mg/kg | 1 ×/wk | 46 | 26 | 77 | <0.0001 |
| Compound A 200 mg/kg | Two 100 mg/kg doses, 8 hr apart 1 ×/wk | 68 | 26 | 162 | <0.0001 |
| Compound A 50 mg/kg | 2 on/5 off × 4, QD | 57 | 26 | 119 | <0.0001 |
| Compound A 80 mg/kg | 5 on/23 off, QD | 59 | 26 | 127 | <0.0001 |
| Compound A 20 mg/kg | 20 on/8 off, QD | 46 | 26 | 77 | <0.0001 |
| Compound A 100 mg/kg | 2 on/12 off × 2, QD | 57 | 26 | 119 | <0.0001 |
| Compound A 50 mg/kg | 4 on/10 off × 2, QD | 55 | 26 | 112 | <0.0001 |
| Compound A 15 mg/kg | QD | 42 | 26 | 62 | <0.0001 |
| Compound A 100 mg/kg | 2 on/5 off × 4, QD | 75 | 26 | 188 | <0.0001 |
| Compound A 30 mg/kg | QD | 59 | 26 | 127 | <0.0001 |
| Compound A 50 mg/k2 | 1 ×/wk | 32 | 26 | 23 | 0.0036 |
| Compound A 7.5 mg/kg | QD | 32 | 26 | 23 | 0.0012 |

Example 2

The antitumor activity of Compound A in the human acute myeloid leukemia xenograft model MOLM-13 in immunocompromised mice using an oral qd×5 schedule was assessed.

A. Test Compound A

Compound A was formulated as an amorphous solid dispersion micro-bulk precipitate (MBP) powder containing 30% drug substance and 70% HPMC-AS polymer was reconstituted immediately before administration as a suspension in Klucel/Tween, and remaining suspension was discarded after dosing. All dose levels are reported as the actual dosage of Compound A rather than including drug plus polymer.

B: In Vivo Assays

Animals

Female SCID:beige mice (10/group), obtained from Charles River Laboratories (Wilmington, Del.) were utilized when they were approximately 8-10 weeks of age and weighed 21-23 g. The health of the mice was assessed daily by gross observation and analyses of blood samples taken from sentinel animals housed on shared shelf racks. All animals were allowed to acclimate and recover from any shipping-related stress for a minimum of 72 hours prior to experimental use. Autoclaved water and irradiated food (5058-ms Pico Lab mouse chow, Purina Mills, Richmond, Ind.) were provided ad libitum, and the animals were maintained on a 12 hour light and dark cycle. Cages, bedding and water bottles were autoclaved before use and changed weekly. All animal experiments were conducted in accordance with the Guide for the Care and Use of Laboratory Animals, local regulations, and protocols approved by the Roche Animal Care and Use Committee in an AAALAC accredited facility.

Tumors

MOLM-13 cells (ATCC) were maintained in RPMI 1640 with L-glutamine (2 mM) media (GIBCO/Invitrogen, Carlsbad, Calif.) supplemented with 10% heat-inactivated Fetal Bovine Serum (HI-FBS; GIBCO/Invitrogen, Carlsbad, Calif.), and 1% 100 mM sodium pyruvate. Each mouse received $1 \times 10^6$ cells suspended in Phosphate Buffered Saline (PBS) intravenously inoculated via the caudal tail vein in a volume of 0.2 ml using a 1 cc syringe and a 26 gauge needle.

Study Design:

The doses selected for Compound A and schedules utilized in this study are shown in Table 5 below.

TABLE 5

Study Design

| Tumor Model | Treatment Groups |
|---|---|
| MOLM-13 | 1. Vehicle qd × 5 po<br>2. Compound A 80 mg/kg<br>5 days qd po (qd × 5), 23 days off |

Treatment

Compound A was administered orally (po) using a 1 cc syringe and 18-gauge gavage needle (02 ml/animal). Treatment duration was initiated on day 3 and was for 2 weeks. Animal body weights were measured three times per week and animals were monitored for clinical signs daily.

Figure 3:
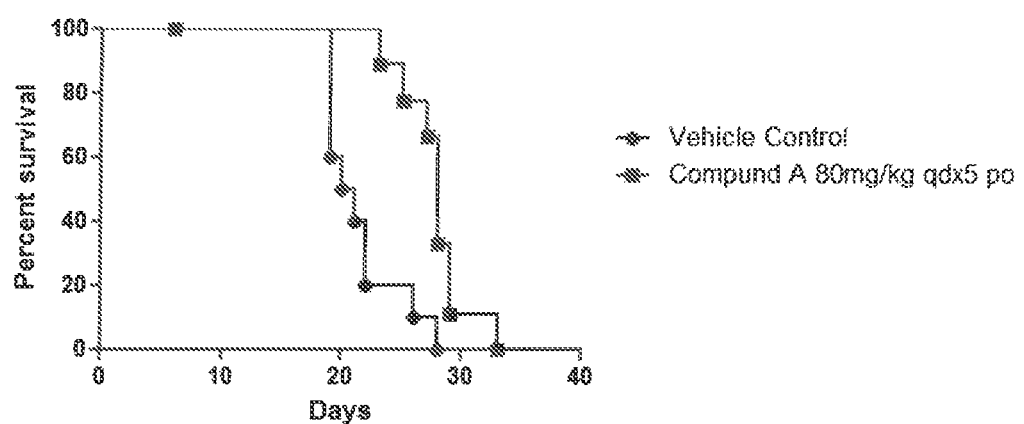
FIG. 3 illustrates the efficacy of Compound A for treating leukemia using the 5 day dosing schedule.

The results of this experiment are summarized Tables 6-7 below and FIG. 3. The 5 day treatment schedule yielded a 37% percent increase in life span (% ILS) in the absence of treatment related toxicity.

TABLE 6

Toxicity Summary

| Group | Frequency | % Change in Body Weight at end of Study Day 17 | Maximum % Weight loss | Maximum % Weight gain | # of animals ≥20% BWL | Mortality (reason) |
|---|---|---|---|---|---|---|
| Vehicle | QD | −4.9 | −6.0 | −2.5 | 0 | 0 |
| Compound A 80 mg/kg | qdx5 | −3.2 | −5.5 | −3.2 | 0 | 1 (dosing injury) |

TABLE 7

Efficacy/Survival Summary

| Group | | 50% Treatment Days | 50% Vehicle days | % ILS | p value |
|---|---|---|---|---|---|
| Vehicle | qd × 5 | — | — | — | — |
| Compound A 80 mg/g | qd × 5 | 28 | 21 | 37 | <0.05 |

Example 3

A. Compound a Composition and Administration

Film-coated tablets containing Compound A at dosage strengths of 10 mg, 50 mg, 200 mg, and 400 mg were developed. The 10 mg tablets contain hypromellose acetate succinate, mannitol, microcrystalline cellulose, croscarmellose sodium, colloidal silicon dioxide, and magnesium stearate. The film-coat consists of hypromellose, titanium dioxide, talc, triacetin, iron oxide yellow, and iron oxide red. The 50 mg, 200 mg, and 400 mg film coated tablets contain the excipients hypromellose acetate succinate, croscarmellose sodium, colloidal silicon dioxide, and magnesium stearate. The film-coat consists of polyvinyl alcohol, titanium dioxide, polyethylene glycol, talc, iron oxide yellow, iron oxide red, and iron oxide black.

The dosage amount can vary and will, of course, have to be adjusted to the individual requirements in each particular case. In the case of oral administration, the dosage can vary from about 100 mg to about 3000 mg per day of Compound A. The daily dosage can be administered as single dose or in divided doses.

B. Clinical Design

By way of nonlimiting examples, patients with advanced solid tumors including colorectal cancer, prostate cancer, lung cancer, kidney cancer and breast cancer were administered Compound A formulated as described above under the following schedules and dosage ranges: (i) 1600-2400 mg total weekly dose (once weekly×3 followed by about 13 days of rest), (ii) 1000 mg total daily dose (daily×3 followed by 25 days of rest), and (iii) 500-800 mg total daily dose (daily×5 followed by 23 days of rest). Tumor biopsies were collected at baseline and cycle 1, day 5±2. The pharmacological effects of Compound A was assessed by measuring biomarker changes between baseline and post treatment C. Biological Assays Biological assay results of the administration of Compound A on patients according to the clinical design schedule and dosage ranges described above are set forth in Tables 8-11. Activity from biomarker assays shows direct p53 activation (Table 5), and anti-proliferative effects Ki67 (Table 6), TUNEL (Table 7), and FLT-PET (Table 8).

TABLE 8

MDM2 mRNA Assay

| Cohort and Schedule | Patient | MDM2 mRNA FCBL | Median FCBL | Average FCBL |
|---|---|---|---|---|
| BM-A1 800 mg bid Qwk × 3 | 1501 | 1.0 | 1.1 | 1.2 |
| | 1701 | 1.4 | | |
| | 1702 | 1.1 | | |
| BM-A2 1200 mg bid Qwk × 3 | 1602 | 1.3 | 1.3 | 1.4 |
| | 1703 | 1.0 | | |
| | 1603 | 1.0 | | |
| | 1201 | 1.8 | | |
| | 1503 | 2.1 | | |
| BM-B1 400 mg bid × 5 d | 2701 | 5.4 | 8.7 | 8.5 |
| | 2502 | 3.7 | | |
| | 2702 | 12.1 | | |
| | 2404 | 12.9 | | |
| BM-B2 500 mg bid × 3 d | 2405 | 0.2 | 1.3 | 5.1 |
| | 2504 | 0.7 | | |
| | 2203 | 1.3 | | |
| | 2204 | 3.8 | | |
| | 2505 | 19.6 | | |
| BM-B3 500 mg qd × 5 d | 2703 | 1.5 | 2.0 | 2.4 |
| | 2506 | 2.5 | | |
| | 2406 | 4.2 | | |
| | 2705 | 1.2 | | |

MDM2 mRNA concentrations from human tumor tissue were assessed by RT PC Treatment with Compound A under the doses below increased the levels of p53 leading to an increase in the levels of MDM2 mRNA expression in patient's tumors. This elevation in the levels of MDM2 mRNA is consistent with activation of the p53 pathway by Compound A.

TABLE 9

Ki-67 Assay

| Cohort and Schedule | Patient | % CBL | Median % CBL | Average % CBL |
|---|---|---|---|---|
| BM-A1 800 mg bid Qwk × 3 | 1501 | 14 | −8.5 | −8.5 |
|  | 1701 | −31 |  |  |
| BM-A2 1200 mg bid Qwk × 3 | 1602 | −33 | −33.0 | −27.8 |
|  | 1703 | −57 |  |  |
|  | 1603 | 30 |  |  |
|  | 1201 | −5 |  |  |
|  | 1503 | −75 |  |  |
| BM-B1 400 mg bid × 5 d | 2701 | −97 | −13.0 | −17.7 |
|  | 2502 | −13 |  |  |
|  | 2404 | 57 |  |  |
| BM-B2 500 mg bid × 3 d | 2503 | 3 | −69.8 | −53.9 |
|  | 2504 | −70 |  |  |
|  | 2204 | −70 |  |  |
|  | 2505 | −79 |  |  |
| BM-B3 500 mg qd × 5 d | 2703 | −67 | −66.5 | −57.1 |
|  | 2506 | −96 |  |  |
|  | 2406 | −8 |  |  |

The Ki-67 protein is a cellular marker for proliferation. It is strictly associated with cell proliferation and can be measured in tissue sections via immunohistochemistry to determine degree of proliferation. Ki-67 protein is present during all active phases of the cell cycle (G1, S, G2, and mitosis), but is absent from resting cells (00). Decrease levels of tumor proliferation in patients were observed via Ki67 after treatment with Compound A under the doses and schedules below. This decrease in proliferation is in response to the p53 activation induced by Compound A.

TABLE 10

TUNEL Assay

| Cohort and Schedule | Patient | TUNEL + cells (mm2) FCBL | Median FCBL | Average FCBL |
|---|---|---|---|---|
| BM-A1 800 mg bid Qwk × 3 | 1501 | 0.8 | 0.8 | 1.2 |
|  | 1701 | 0.8 |  |  |
|  | 1601 | 3.2 |  |  |
|  | 1702 | 0.1 |  |  |
| BM-A2 1200 mg bid Qwk × 3 | 1602 | 5.3 | 2.3 | 2.7 |
|  | 1703 | 2.3 |  |  |
|  | 1603 | 0.9 |  |  |
|  | 1201 | 1.6 |  |  |
|  | 1503 | 3.3 |  |  |
| BM-B1 400 mg bid × 5 d | 2701 | 0.9 | 1.8 | 1.7 |
|  | 2601 | 1.8 |  |  |
|  | 2502 | 1.8 |  |  |
|  | 2702 | 0.9 |  |  |
|  | 2404 | 3.2 |  |  |
| BM-B2 500 mg bid × 3 d | 2405 | 0.5 | 0.9 | 1.7 |
|  | 2503 | 0.4 |  |  |
|  | 2504 | 0.6 |  |  |
|  | 2203 | 5.3 |  |  |
|  | 2204 | 1.2 |  |  |
|  | 2505 | 1.9 |  |  |
| BM-B3 500 mg qd × 5 d | 2703 | 0.6 | 1.2 | 1.2 |
|  | 2506 | 1.7 |  |  |
|  | 2406 | 1.2 |  |  |

Tumor biopsy cells were analyzed via TUNEL (terminal deoxynucleotidyl transferase dUTP nick end labeling) to determine cell apoptosis. TUNEL is a common method for detecting DNA fragmentation that results from apoptotic signaling cascades. The assay relies on the presence of nicks in the DNA which can be identified by terminal deoxynucleotidyl transferase or TdT, an enzyme that will catalyze the addition of dUTPs that are secondarily labeled with a marker. Treatment with Compound A lead to an increase in apoptosis and this is in response to the p53 activation induced by Compound A.

TABLE 11

FLT PET Assay

| Cohort and Schedule | Patient | % CBL Cycle 1 | Median % CBL | Average % CBL |
|---|---|---|---|---|
| BM-A1 800 mg bid Qwk × 3 | 1407 | −19.0 | −20.5 | −17.0 |
|  | 1501 | −11.7 |  |  |
|  | 1701 | −28.5 |  |  |
|  | 1408 | −21.9 |  |  |
|  | 1601 | −29.5 |  |  |
|  | 1702 | 8.9 |  |  |
| BM-A2 1200 mg bid Qwk × 3 | 1602 | −5.0 | 3.2 | −0.9 |
|  | 1703 | 21.1 |  |  |
|  | 1603 | −31.1 |  |  |
|  | 1201 | 11.3 |  |  |
|  | 1503 | −73.1 |  |  |
| BM-B1 400 mg bid × 5 d | 2701 | −82.5 | −32.2 | −43.4 |
|  | 2501 | −49.7 |  |  |
|  | 2502 | −29.3 |  |  |
|  | 2702 | −23.4 |  |  |
|  | 2404 | −32.2 |  |  |
| BM-B2 500 mg bid × 3 d | 2405 | −34.9 | −34.9 | −39.2 |
|  | 2504 | −62.4 |  |  |
|  | 2203 | −24.7 |  |  |
|  | 2204 | −19.4 |  |  |
|  | 2505 | −54.5 |  |  |
| BM-B3 500 mg qd × 5 d | 2703 | −56.4 | −31.0 | −29.04 |
|  | 2704 | −34.3 |  |  |
|  | 2205 | −21.7 |  |  |
|  | 2506 | −31 |  |  |
|  | 2406 | −1.8 |  |  |

FLT PET imaging scan was used to analyze tumor proliferation in patients undergoing treatment with Compound A under the doses and schedules set forth below. A negative percent change from baseline is indicative of an antiproliferative effect. This is in alignment with the Ki67 and TUNEL results. By FLT PET, an antiproliferative effects was seen in all doses tested in particular the qd×3 days and qd×5 day schedules.

What is claimed:

1. A method of treating a patient suffering from cancer, comprising administering to said patient a pharmaceutical composition containing as an active ingredient 4-{[(2R, 3S, 4R, 5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound A) in an amount from about 400 mg/day to about 1600 mg/day, daily, for up to about 7 days, followed by a rest period of about 21 days, said administration starting on the first day of a 28 day treatment cycle, wherein said cancer is a solid tumor.

2. A method of treating a patient suffering from cancer, comprising administering to said patient a pharmaceutical composition containing as an active ingredient 4-{[(2R, 3S, 4R, 5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound A) in an amount from about 400 mg/day to about 1600 mg/day, daily, for up to about 5 days, followed by a rest period of about 23 days, said administration starting on the first day of a 28 day treatment cycle, wherein said cancer is a solid tumor.

3. The method of claim 2 wherein Compound A is administered in an amount from about 400 mg/day to about 1200 mg/day.

4. The method of claim 1 wherein the treatment cycle being repeated every 28 days for up to about 12 cycles.

5. The method of claim 1 wherein Compound A is administered twice daily in equal doses.

6. The method of claim 1 wherein the cancer is selected from the group consisting of colon, breast, prostate, head, neck, lung, kidney and colorectal.

7. The method of claim 2, comprising administering to said patient a pharmaceutical composition containing as an active ingredient Compound A at about 500 mg/day total, daily for up to about 5 days, followed by a rest period of about 23 days, said administration starting on the first day of a 28 day treatment cycle.

8. The method of claim 7 wherein the cancer is selected from the group consisting of colon, breast, prostate, head, neck, lung, kidney, melanoma, soft tissue sarcoma colorectal and osteosarcoma.

9. A method of treating a patient suffering from leukemia, comprising administering to said patient a pharmaceutical composition containing as an active ingredient 4-{[2R, 3S, 4R, 5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound A) at about 1200 mg/day total daily, for up to about 5 days, followed by a rest period of about 23 days, said administration starting on the first day of a 28 day treatment cycle.

10. A method of treating a patient suffering from cancer, comprising administering to said patient a pharmaceutical composition containing as an active ingredient 4-{[2R, 3S, 4R, 5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound A) in an amount of about 400-1000 mg total daily dose for up to 3 days followed by a rest period of up to about 25 days, said administration starting on the first day of a 28 day treatment cycle.

11. The method of claim 10 wherein the cancer is selected from the group consisting of colon, breast, prostate, head, neck, lung, kidney, melanoma, soft tissue sarcoma, colorectal and osteosarcoma.

* * * * *